US00PP25046P3

(12) United States Plant Patent
Johnson

(10) Patent No.: US PP25,046 P3
(45) Date of Patent: Nov. 11, 2014

(54) ***AZALEA* PLANT NAMED 'ROBLEV'**

(50) Latin Name: ***Azalea* hybrid**
Varietal Denomination: ROBLEV

(71) Applicant: Flint Jerome Johnson, Mobile, AL (US)

(72) Inventor: Flint Jerome Johnson, Mobile, AL (US)

(73) Assignee: PDSI, Loxley, AL (US)

( * ) Notice: Subject to any disclaimer, the term of this patent is extended or adjusted under 35 U.S.C. 154(b) by 0 days.

(21) Appl. No.: 13/694,811

(22) Filed: Jan. 7, 2013

(65) Prior Publication Data

US 2014/0196183 P1 Jul. 10, 2014

(51) Int. Cl.
*A01H 5/00* (2006.01)

(52) U.S. Cl.
USPC ..... Plt./238

(58) Field of Classification Search
USPC ..... Plt./238
See application file for complete search history.

*Primary Examiner* — Anne Grunberg
(74) *Attorney, Agent, or Firm* — Cassandra Bright

(57) ABSTRACT

A new and distinct *Azalea* cultivar named 'ROBLEV' is disclosed, characterized by distinctive solid white flowers. Plants are, globular, very compact and bloom throughout Spring, Summer and Fall. The new cultivar is a *Azalea*, suitable for ornamental garden purposes.

2 Drawing Sheets

Figure 1:
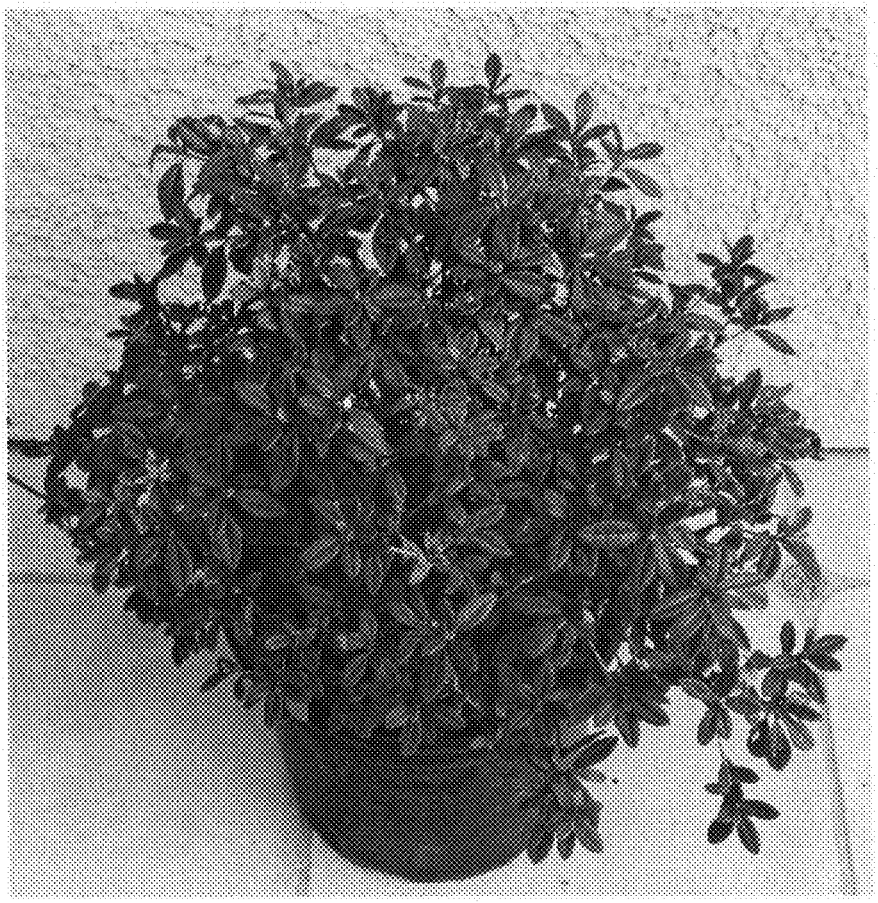

Latin name of the genus and species: *Azalea* hybrid.
Variety denomination: 'ROBLEV'.

BACKGROUND OF THE INVENTION

The new cultivar is a product of chance discovery by the inventor. This new variety, hereinafter referred to as 'ROBLEV', was discovered as a branch sport by Flint Jerome Johnson, Jul. 23, 2005, in Loxley, Ala., at a commercial nursery. The parent variety producing this naturally occurring mutation is *Azalea* 'Robled' U.S. Plant Pat. No. 15,862.

After identifying the new variety as a potentially interesting selection, the inventor first organized propagation of 'ROBLEV' by vegetative cuttings on Jun. 2, 2006 at the same commercial nursery in Loxley, Ala. The inventor continued controlled testing and propagation, assessing stability of the unique characteristics of this variety. Multiple generations have been reproduced and have shown that the unique features of this cultivar are stable and reproduced true to type.

SUMMARY OF THE INVENTION

The cultivar 'ROBLEV' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'ROBLEV' These characteristics in combination distinguish 'ROBLEV' as a new and distinct *Azalea* cultivar:

1. The unique spring, summer, and fall blooming.
2. Solid white flowers
3. Easily propagated with semi-hardwood cuttings in late spring through the summer.
4. Good specimen plant.
5. Excellent performance in planters.
6. Very good foundation plant.
7. Does well as an understory plant in a woodland garden.
8. Hardy to Zone 7.

9. Attracts butterflies.
10. Very compact growth
11. Uniform, globular plant shape.

COMPARISON TO PARENT VARIETY

'ROBLEV' is similar in most horticultural characteristics to the parent variety *Azalea* hybrid 'Robled', U.S. Plant Pat. No. 15,862. Plants of the new cultivar 'ROBLEV' however, produce flowers that are white in coloration, compared to the pink flowers of the parent variety. Pedicel coloration is also different. Additionally, the mature plant height and spread of the new variety is less than that of the parent variety. Plant habit is overall more compact in the new variety, compared to the parent.

COMMERCIAL COMPARISON

'ROBLEV' can be compared to the commercial variety *Azalea* hybrid 'ROBLEX' filed concurrently with this application, having application Ser. No. 13/694,812. Plants of the new cultivar 'ROBLEV' are similar to plants of 'ROBLEX' in most horticultural characteristics, however, plants of the new cultivar 'ROBLEV' produce flowers that are completely white, without the characteristic occasional pink stripe found on flowers of 'ROBLEX'. Additionally, foliage of 'ROBLEV' is smaller and plants of 'ROBLEV' are more compact than plants of 'ROBLEX'.

'ROBLEV' can be compared to the commercial variety *Azalea* hybrid 'ROBLEG' U.S. Plant Pat. No. 15,227. Plants of the new cultivar 'ROBLEV' are similar to plants of 'ROBLEG' in most horticultural characteristics, however, plants of the new cultivar 'ROBLEV' produce flowers that are completely white, without the characteristic occasional Yellow-Green dotting found on flowers of 'ROBLEG'. Additionally, plants of 'ROBLEV' are more compact than plants of 'ROBLEG'.

BRIEF DESCRIPTION OF THE PHOTOGRAPHS

The accompanying photograph in FIG. 1 illustrates in full color a typical plant of 'ROBLEV' grown outdoors in Alabama. The plant is approximately 2 years old, and is shown in a three gallon container.

Figure 2:
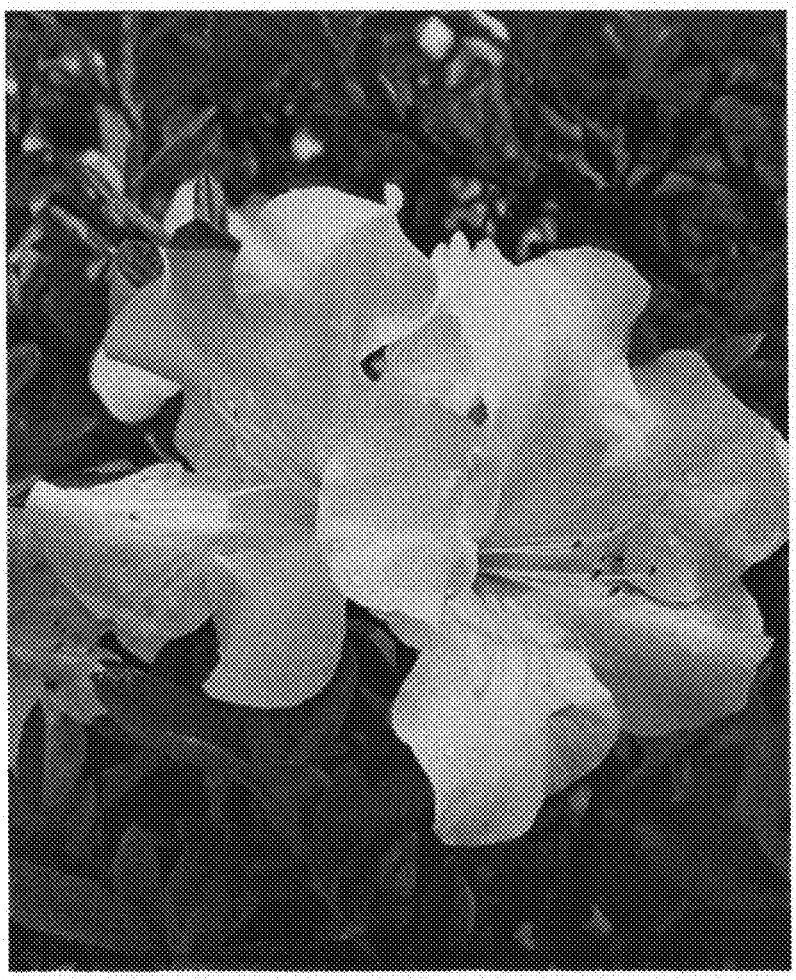

FIG. 2 shows a close up of typical flowers of the new variety.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2001 except where general terms of ordinary dictionary significance are used. The following observations and measurements describe 'ROBLEX' plants grown outdoors in Loxley, Ala. Plants are approximately 2 years old, in a 3 gallon nursery container. Measurements and numerical values represent averages of typical plant types.

Botanical classification: *Rhododendron* hybrid 'ROBLEV'.

PROPAGATION

Typically by semi-hardwood cuttings in Spring and Summer.

PLANT

Growth habit: Compact evergreen shrub. Slow to moderate growth rate.

Height: Approximately 36 cm to top of foliar and flowering plane.

Plant spread: Approximately 58 cm.

Branching characteristics: Well branched, approximately 12 primary branches from center of plant, angled approximately 75° from center of plant. Each primary branches has 6 to 10 lateral branches.

Primary branches:

- *Length of primary branches*.—Approximately 15 cm to 30 cm.
- *Diameter of primary branches*.—Approximately 0.65 cm.
- *Primary branch strength*.—Very strong, difficult to break.
- *Primary branch color*.—Near RHS Yellow-Green N144B, with age, covered with a thin bark like layer colored near Grey-Orange 177B.
- *Primary branch texture*.—Young growth hirsute, hairs approximately 0.15 cm long, colored near Greyed-Orange 166C. Older growth scaly, pubescent, hairs appressed. Hairs colored near Greyed-Orange 166C.

Lateral branches:

- *Number of lateral branches*.—Approximately 6 to 10 per primary branch.
- *Length of lateral branches*.—Average 12 cm.
- *Diameter of lateral branches*.—Average 0.4 cm.
- *Lateral branch strength*.—Very strong, flexible.
- *Lateral branch color*.—Near RHS Yellow-Green N144C.
- *Lateral branch texture*.—Hirsute. Hairs colored near Greyed-Orange 166C.

Internode length: Range between 0.5 to 3.5 cm.

Age of plant described: Approximately 2 years.

FOLIAGE

Leaf:

- *Type*.—Simple.
- *Arrangement*.—Alternate.
- *Average length*.—Approximately 4.5 cm.
- *Average width*.—Approximately 1.5 cm.
- *Shape of blade*.—Elliptic.
- *Apex*.—Acute, short mucronte.
- *Base*.—Attenuate.
- *Attachment*.—Stalked.
- *Margin*.—Entire.
- *Texture of top surface*.—Highly pubescent. Hairs appressed.
- *Texture of bottom surface*.—Pubescent. More hairs present along main vein and margin.
- *Foliage scent*.—None.
- *Color*.—Young foliage upper side: Near RHS Green 137B. Young foliage under side: Near RHS Green 138B. Mature foliage upper side: Near RHS Green 138A. Mature foliage under side: Near RHS Green 138A.

Venation:

- *Type*.—Pinnate.
- *Venation color upper side*.—Near RHS Yellow-Green 151A.
- *Venation color under side*.—Near RHS Yellow-Green 153A.

Petiole:

- *Length*.—About 1.3 cm.
- *Diameter*.—About 0.25 cm.
- *Color*.—Near RHS Yellow-Green N144C, upper and lower surfaces.

FLOWER

Bloom period: Plants begin flowering in the Spring, around late March, and continue to produce flowers throughout Summer and Fall. Flowering ends with frost, typically October or November.

Arrangement: Axillary clusters of perfect, open funnel shaped individual flowers. Typically 4 to 10 flowers per cluster.

Inflorescence:

- *Height*.—Average 9.0 cm.
- *Diameter*.—Average 8.5 cm.

Peduncle: No peduncle, clusters arise directly from axils.

Pedicel:

- *Length*.—Average 0.8 cm.
- *Diameter*.—0.2 cm.
- *Color*.—Near RHS Yellow-Green 145C.
- *Texture*.—Densely pubescent.
- *Aspect*.—Straight to very slightly curved. Angle of attachment, approximately 45° angle from axil.

Flowers:

- *Length*.—Average 4.5 cm.
- *Diameter*.—Average 3.5 cm.
- *Facing direction*.—Outwardly and upwardly facing.
- *Persistent or self-cleaning*.—Petals self cleaning.
- *Fragrance*.—None.
- *Tube*.—Tube length: Approximately 1.5 cm. Tube width a widest point: Approximately 1.0 cm. Tube width and narrowest point: Approximately 0.5 cm.

*Petals*.—Unfused petal segments: Length: Approximately 2.0 cm. Width: Approximately 1.8 cm. Apex: Retuse. Shape of petal: Unfused portion, obovate. Petal margin: Entire. Ruffled aspect along margin. Petal Arrangement: Approximately ⅓ fused from base. Petal Number: 5. Petal Texture: Smooth.

*Color*.—Inner surface at first opening: Near RHS Green-White 157D. Outer surface at first opening: Near RHS Green-White 157D. Inner surface at maturity: Near RHS White 155C. Outer surface at maturity: Near RHS White 155C. Inner surface at fading: Near RHS White 155B. Outer surface at fading: Near RHS White 155D.

Bud:

*Shape*.—Elliptic.

*Length*.—2.4 cm.

*Diameter*.—1.1 cm.

*Color*.—Near RHS Green-White 157D, at color first showing.

Calyx/sepals:

*Quantity per flower*.—5 sepals.

*Shape*.—Narrow deltate.

*Length*.—0.5 cm.

*Width*.—0.2 cm.

*Apex*.—Acute.

*Base*.—Fused.

*Margin*.—Entire.

*Texture*.—Highly pubescent.

*Color*.—Inner Surface: Near RHS Yellow-Green 145C. Outer Surface: Near RHS Yellow-Green 145B.

REPRODUCTIVE ORGANS

Stamens:

*Number*.—10.

*Length*.—3.1 cm.

*Width*.—0.1 cm.

*Color*.—Near RHS White 155D.

*Anthers*.—Length: Approximately 0.2 cm. Color: Near RHS Greyed-Orange N167A. Pollen: Not observed to date.

Pistil:

*Number*.—1.

*Length*.—5.6 cm.

*Style*.—Length: 3.7 cm. Color: Near RHS White 155D.

*Stigma*.—Globular, colored near Yellow-Green 154C.

*Ovary*.—Sericeous texture. Approximately 0.3 cm in diameter. Colored near Yellow-Green 144C. Hairs colored near White N155A.

OTHER CHARACTERISTICS

Disease and pest resistance: Not observed to be susceptible nor resistant to normal diseases and pests of *Azalea* hybrid.

Temperature tolerance: USDA Zone 6.

Fruit/seed production: Not observed to date.

What is claimed is:

1. A new and distinct cultivar of *Azalea* plant named 'ROB-LEV' as herein illustrated and described.

* * * * *